US012635987B2

(12) United States Patent
Matsumoto

(10) Patent No.: US 12,635,987 B2
(45) Date of Patent: May 26, 2026

(54) IMAGE GENERATION DEVICE, IMAGE GENERATION METHOD, AND PROGRAM

(71) Applicant: Konica Minolta, Inc., Tokyo (JP)

(72) Inventor: Hiroaki Matsumoto, Yokohama (JP)

(73) Assignee: Konica Minolta, Inc., Tokyo (JP)

( * ) Notice: Subject to any disclaimer, the term of this patent is extended or adjusted under 35 U.S.C. 154(b) by 120 days.

(21) Appl. No.: 17/734,166

(22) Filed: May 2, 2022

(65) Prior Publication Data

US 2022/0370045 A1     Nov. 24, 2022

(30) Foreign Application Priority Data

May 24, 2021     (JP) ................................. 2021-086809

(51) Int. Cl.
A61B 8/00          (2006.01)

(52) U.S. Cl.
CPC ............ A61B 8/5207 (2013.01); A61B 8/463 (2013.01); A61B 8/469 (2013.01)

(58) Field of Classification Search
CPC ...... A61B 8/5207; A61B 8/5253; A61B 8/463
See application file for complete search history.

(56) References Cited

U.S. PATENT DOCUMENTS

2020/0202518 A1 *   6/2020   Vignon ................ A61B 8/4245

FOREIGN PATENT DOCUMENTS

| JP | 2004-522515 A | 7/2004 |
| JP | 2014138847 A | 7/2014 |
| JP | 2016539707 A | 12/2016 |
| JP | 2018198799 A | 12/2018 |
| JP | 2021058232 A | 4/2021 |
| JP | 2021069793 A | 5/2021 |

OTHER PUBLICATIONS

Perez-Gonzalez et al., "Deep Learning Spatial Compounding from Multiple Fetal Head Ultrasound Acquisitions," (Oct. 1, 2020), ASMUS 2020, PIPPI 2020: Medical Ultrasound, and Preterm, Perinatal and Paediatric Image Analysis pp. 305-314. (Year: 2020).*
Perez-Gonzalez et al., "Spatial Compounding of 3-D Fetal Brain Ultrasound Using Probabilistic Maps," ( Jan. 2018), vol. 44, Issue 1, Jan. 2018, pp. 278-291. (Year: 2018).*
Japanese Office Action (JPOA) dated Oct. 11, 2024 issued for Japanese patent application No. 2021-086809 and its English machine translation.
Japanese Office Action (JPOA) dated Mar. 18, 2025 for Japanese Patent Application No. 2021-086809; English translation.

* cited by examiner

*Primary Examiner* — Keith M Raymond
(74) *Attorney, Agent, or Firm* — RANKIN, HILL & CLARK LLP

(57)          ABSTRACT

An image generation device includes: an image acquirer that acquires a plurality of ultrasound images generated on the basis of a plurality of reception signals respectively corresponding to reflected ultrasound waves of transmission ultrasound waves transmitted in a plurality of different transmission directions; an identification result acquirer that acquires an identification result output from a discriminator by inputting the plurality of ultrasound images that has been acquired to the discriminator, the discriminator identifying an object to be identified included in the input ultrasound images; and an image combiner that generates a composite image on the basis of the plurality of ultrasound images and the identification result.

13 Claims, 10 Drawing Sheets

51, 50

FIRST REFERENCE DATA (K×K)

52, 50

SECOND REFERENCE DATA (K×K)

PROCESSING FOR GENERATING
IDENTIFICATION MODEL

RECEIVE DESIGNATION OF
ULTRASOUND IMAGE FOR TRAINING ~S101

RECEIVE DESIGNATION OF LABEL ~S102

SET FIRST IMAGE (K×K) ~S103

EXTRACT SECOND IMAGE (N×N) ~S104

ACQUIRE FEATURE AMOUNT
OF SECOND IMAGE ~S105

ASSOCIATE FEATURE AMOUNT
WITH CERTAINTY FACTOR ~S106

TRAIN IDENTIFICATION MODEL ~S107

END

IMAGE GENERATION DEVICE, IMAGE GENERATION METHOD, AND PROGRAM

The entire disclosure of Japanese patent Application No. 2021-086809, filed on May 24, 2021, is incorporated herein by reference in its entirety.

BACKGROUND

Technological Field

The present disclosure relates to an image generation device, an image generation method, and a program for generating a medical image.

Description of the Related Art

Conventionally, such an ultrasound diagnostic apparatus is known that includes an ultrasound probe including an array of a large number of transducers, transmits and receives ultrasound waves to and from a subject such as a living body, generates ultrasound image data on the basis of a signal obtained from the received ultrasound waves, and displays an ultrasound image based on the ultrasound image data on an image display device. The ultrasound diagnosis imaging using the apparatus described above can be repeatedly performed because it is non-invasive and highly safe and can obtain the state of the subject such as the heartbeat, the fetal movement, or the like in real time by a simple operation of applying the ultrasound probe to the body surface of the subject.

However, an image obtained by such an ultrasound diagnostic apparatus includes various kinds of noise and speckles generated by interference phenomenon of a reception signal obtained from ultrasound waves received by the ultrasound probe as well as information regarding a tissue in the subject. The noise and speckles included in the image often impede accurate recognition of the position and shape of the boundary between tissues in the subject.

In recent years, an ultrasound diagnostic apparatus using, for example, spatial compounding has become widespread as a method for reducing such noise and speckles. The spatial compounding is a method of transmitting and receiving ultrasound waves to and from the same position of the subject in a plurality of different directions at the same time, and performing average superposition of a plurality of pieces of acquired ultrasound image data. As a result, in a case where, for example, N pieces of ultrasound image data are obtained, noise and speckles are reduced by the square root of N in composite image data obtained by combining the N pieces of ultrasound image data.

In addition, according to the spatial compounding, performance of extracting an anisotropic part can be improved. The anisotropic part means a site where the intensity of the reception signal due to scattering, reflection, and the like upon incidence of the ultrasound wave varies depending on angles. Specifically, the anisotropic part indicates a site in a fibrous soft tissue having a reflection intensity not as high as that of a bone surface but exhibiting specular reflection characteristics, such as a tendon or a ligament in a skeletal muscle inside the subject.

An ultrasound diagnostic apparatus using such spatial compounding is disclosed in, for example, JP 2004-522515 A. JP 2004-522515 A discloses a technique capable of generating a higher-quality ultrasound image by synthesizing a mean value, a maximum value, a minimum value, a median value, and the like of pixel values of ultrasound images obtained by reflection signals from a plurality of directions with a control signal selected according to a type of diagnostic inspection for visualizing a target with higher image quality.

With the technique disclosed in JP 2004-522515 A, when, for example, a nerve is targeted, a reception signal from the nerve is amplified, so that the nerve can be visualized with high image quality. However, in the technique disclosed in JP 2004-522515 A, an element other than the nerve, for example, noise or a reception signal from another structure that does not need to be visualized, is also amplified, and as a result, the image quality of the entire ultrasound image may be deteriorated.

SUMMARY

An object of the present disclosure is to provide an image generation device, an image generation method, and a program with which it is possible to generate a medical image including a specific object to be identified with high image quality using spatial compounding.

To achieve the abovementioned object, according to an aspect of the present invention, an image generation device reflecting one aspect of the present invention comprises: an image acquirer that acquires a plurality of ultrasound images generated on the basis of a plurality of reception signals respectively corresponding to reflected ultrasound waves of transmission ultrasound waves transmitted in a plurality of different transmission directions; an identification result acquirer that acquires an identification result output from a discriminator by inputting the plurality of ultrasound images that has been acquired to the discriminator, the discriminator identifying an object to be identified included in the input ultrasound images; and an image combiner that generates a composite image on the basis of the plurality of ultrasound images and the identification result.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Figure 1:
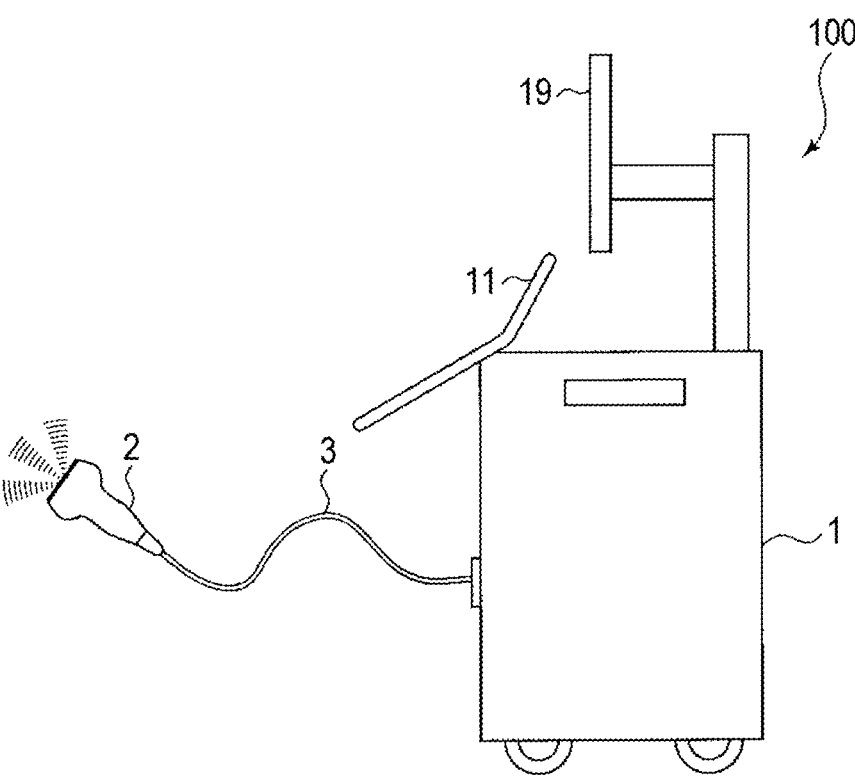
FIG. 1 is a diagram illustrating an example of a configuration of an ultrasound diagnostic apparatus.

Hereinafter, one or more embodiments of the present invention will be described with reference to the drawings. However, the scope of the invention is not limited to the disclosed embodiments. In the following description, components having the same functions and configurations are denoted by the same reference numerals, and the description thereof will be omitted.

Configuration

[Ultrasound Diagnostic Apparatus 100]

FIG. 1 is a diagram illustrating an example of a configuration of an ultrasound diagnostic apparatus 100. As illustrated in FIG. 1, the ultrasound diagnostic apparatus 100 includes an image generation device 1 and an ultrasound probe 2. The ultrasound probe 2 transmits an ultrasound wave (transmission ultrasound wave) to a subject and receives a reflected wave (reflected ultrasound wave: echo) of the ultrasound wave reflected in the subject. In the following description, a living body such as a human body is used as an example of the subject.

The image generation device 1 is connected to the ultrasound probe 2 via a cable 3, and transmits a drive signal which is an electric signal to the ultrasound probe 2 to cause the ultrasound probe 2 to transmit a transmission ultrasound wave to the subject. Then, the image generation device 1 forms an ultrasound image of an internal state of the subject on the basis of a reception signal that is an electric signal generated by the ultrasound probe 2 according to the reflected ultrasound wave from the inside of the subject received by the ultrasound probe 2.

The ultrasound probe 2 includes a transducer 2a (see FIG. 2) including a plurality of piezoelectric elements, and a plurality of the transducers 2a is arranged in a one-dimensional array in a lateral direction (scanning direction), for example. The number of transducers 2a can be freely set.

[Image Generation Device 1]

Figure 2:
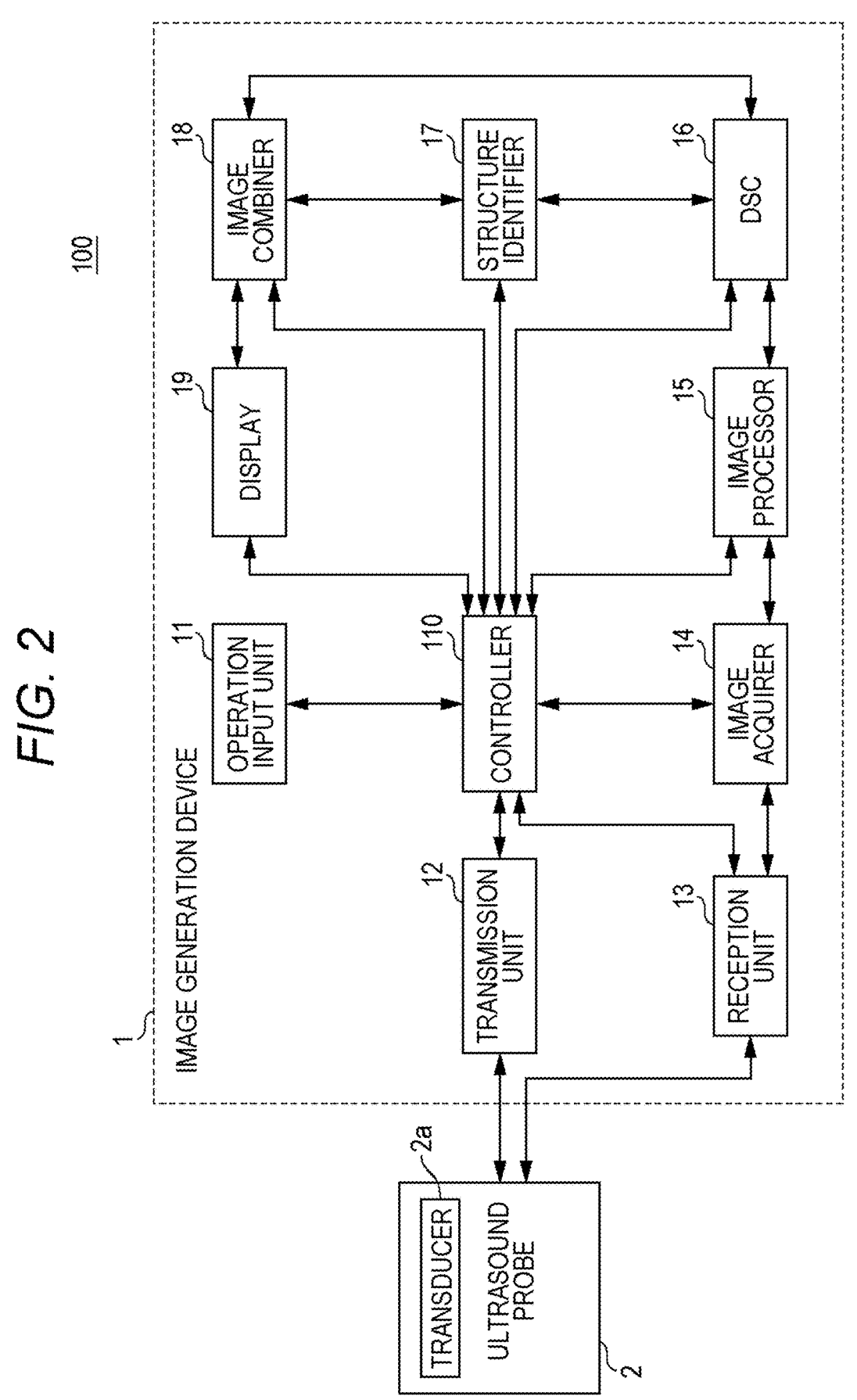
FIG. 2 is a block diagram illustrating an example of a configuration of an image generation device.

FIG. 2 is a block diagram illustrating a configuration example of the image generation device 1. As illustrated in FIG. 2, the image generation device 1 includes, for example, an operation input unit 11, a transmission unit 12, a reception unit 13, an image acquirer 14, an image processor 15, a digital scan converter (DSC) 16, a structure identifier 17, an image combiner 18, a display 19, and a controller 110.

The operation input unit 11 is, for example, an operation device for inputting a command instructing start of diagnosis, data such as information regarding a subject, and the like, and specifically includes, for example, various switches, buttons, a trackball, a mouse, a keyboard, etc. The operation input unit 11 outputs an operation signal based on the input operation to the controller 110.

The transmission unit 12 is a circuit that supplies a drive signal which is an electric signal to the ultrasound probe 2 via the cable 3 and causes the ultrasound probe 2 to generate a transmission ultrasound wave under the control of the controller 110. The transmission unit 12 includes, for example, a clock generation circuit, a delay circuit, and a pulse generation circuit (not illustrated). The clock generation circuit generates a clock signal that determines a transmission timing and a transmission frequency of the drive signal. The delay circuit sets a delay time for each individual path corresponding to each transducer 2a, delays transmission of the drive signal by the set delay time, and performs focusing (transmission beamforming) of a transmission beam including transmission ultrasound waves and setting (steering) of an angle of the transmission beam. The pulse generation circuit generates a pulse signal as a drive signal at a predetermined cycle.

The transmission unit 12 configured as described above drives, for example, some (for example, several tens of) consecutive transducers 2a from among the plurality of (for example, a hundred and several tens to two hundreds and several tens) transducers 2a arrayed in the ultrasound probe 2 to generate a transmission ultrasound wave. Then, the transmission unit 12 performs scanning by changing the transducer 2a to be driven in the lateral direction every time the transmission ultrasound wave is generated. Furthermore, the transmission unit 12 can receive a plurality of reflection signals having different angles by performing scanning while appropriately changing the angle of the transmission beam. In the following description, the angle of the transmission beam that is appropriately changed is referred to as a steering angle.

The reception unit 13 is a circuit that receives a reception signal which is an electric signal from the ultrasound probe 2 via the cable 3 under the control of the controller 110. The reception unit 13 includes, for example, an amplifier, an A/D conversion circuit, and a phasing addition circuit. The amplifier is a circuit for amplifying the reception signal with a preset amplification factor for each individual path corresponding to each transducer 2a. The A/D conversion circuit performs analog/digital conversion (A/D conversion) on the amplified reception signal. The phasing addition circuit gives a delay time to the A/D-converted reception signal for each individual path corresponding to each transducer 2a to adjust the time phase, and adds (phasing addition) the resultant reception signals to generate sound ray data. That is, the phasing addition circuit performs reception beamforming on the reception signal for each transducer 2a to generate sound ray data.

Under the control of the controller 110, the image acquirer 14 performs envelope detection processing, logarithmic compression, and the like on the sound ray data input from the reception unit 13, and performs luminance conversion by adjusting a dynamic range and a gain, thereby generating a B-mode ultrasound image. In the B-mode ultrasound image, the intensity of the reception signal is represented by luminance. Note that, in the present embodiment, the image acquirer 14 may be able to generate an A-mode image (amplitude image), an M-mode image (motion image), and an ultrasound image by a Doppler method, in addition to the B-mode image. In the following, a case where the B-mode ultrasound image is to be processed will be described, and the B-mode ultrasound image will be simply referred to as an ultrasound image. However, in the image generation device 1 according to the present disclosure, an image other than the B-mode ultrasound image may also be set as an object to be processed.

In addition, when the ultrasound probe 2 scans in a plurality of directions while changing angles, the image acquirer 14 generates a plurality of ultrasound images on the basis of a plurality of reflection signals having different angles. The scanning regions are partly or entirely overlap each other among the plurality of pieces of ultrasound image data generated in this manner. The plurality of pieces of ultrasound image data is combined by the image combiner 18.

The image processor 15 performs various types of image processing on the plurality of pieces of ultrasound image data generated by the image acquirer 14.

The DSC 16 performs scanning frequency conversion or the like on the plurality of ultrasound images output from the image processor 15, and converts the ultrasound images into an image signal in a format that can be displayed on the display 19 under the control of the controller 110.

The structure identifier 17 identifies a specific structure (target) in the ultrasound image input from the DSC 16, the controller 110, or the image combiner 18. The structure identifier 17 is an example of an identification result acquirer in the present disclosure. The target is a structure to be clearly and visually recognized by a user of the ultrasound diagnostic apparatus 100 at the time of diagnosis using the ultrasound diagnostic apparatus 100, and is an example of an object to be identified in the present disclosure.

Examples of the target include a plurality of types of structures such as a nerve, a fascia, a blood vessel, and a puncture needle. The puncture needle indicates a needle that is pierced into a living body for collecting tissue or that is used for injecting a liquid medicine into a living body. The target may be appropriately set from among a plurality of types of structures that can be set as a target by a user's operation via the operation input unit 11, or any structure may be determined as a target in advance. The structure identifier 17 may identify one target or a plurality of targets. Specifically, only the nerve may be set as the target, or the nerve and the puncture needle may be set as the target.

The structure identifier 17 includes an identification model that is a learning model subjected to machine learning in advance to identify a target. The identification model is an example of a discriminator and a trained discriminator in the present disclosure. For example, the identification model is constructed by supervised machine learning in which a relationship between the feature amount (for example, the luminance array) of the ultrasound image and information regarding a certainty factor of the target is trained as training data using a known machine learning algorithm (so-called deep learning) such as a neural network. When there are multiple structures that can be set as a target, the identification model may be generated for each target, or one discriminator may identify the multiple structures. The identification model included in the structure identifier 17 is an example of a trained discriminator in the present disclosure.

The certainty factor is an index indicating the likelihood that a certain region in the ultrasound image is the target, and is an example of an identification result in the present disclosure. The certainty factor of the target and a region around the target is large, and the certainty factor of a region other than the target and the region around the target (non-target) is small. The certainty factor is generated for each pixel of the ultrasound image, for example.

The structure identifier 17 generates a certainty factor image corresponding to the input ultrasound image on the basis of the output of the identification model. The certainty factor image is obtained by plotting the certainty factor for each pixel of the ultrasound image and indicates the distribution of the certainty factors with respect to the entire ultrasound image. The detail of the structure identifier 17 will be described later.

The image combiner 18 combines the plurality of ultrasound images generated by the image acquirer 14 to generate a composite image. In particular, the image combiner 18 generates a spatial compounding image obtained by combining portions overlapping each other among a plurality of ultrasound images generated on the basis of a plurality of reflection signals based on transmission beams transmitted at a plurality of steering angles. In the following description, a plurality of ultrasound images generated based on a plurality of reflection signals received from transmission beams transmitted at a plurality of steering angles will be referred to as a plurality of ultrasound images having different steering angles.

When combining a plurality of ultrasound images having different steering angles with each other, the image combiner 18 weights each ultrasound image on the basis of the certainty factor image input from the structure identifier 17. As a result, the image combiner 18 can output the spatial compounding image in which the target is emphasized. The detail of the processing for combining the plurality of ultrasound images by the image combiner 18 will be described later.

The display 19 is a display device such as a light-emitting diode (LED), a liquid crystal display (LCD), a cathode-ray tube (CRT) display, an organic electronic luminescence (EL) display, an inorganic EL display, or a plasma display. The display 19 displays the composite image output from the image combiner 18 under the control of the controller 110. In addition, the display 19 may display a final certainty factor image (the detail of which will be described later) output from the structure identifier 17.

The controller 110 includes, for example, a central processing unit (CPU), a read only memory (ROM), and a random access memory (RAM), reads various processing programs such as a system program stored in the ROM, develops the programs in the RAM, and centrally controls the operation of each unit of the ultrasound diagnostic apparatus 100 in accordance with the developed programs.

The ROM includes a nonvolatile memory such as a semiconductor, and stores a system program corresponding to the ultrasound diagnostic apparatus 100, various processing programs executable on the system program, various data such as a gamma table, and the like. These programs are stored in the form of computer readable program codes, and the CPU sequentially executes operations according to the program codes. The RAM forms a work area in which various programs executed by the CPU and data related to these programs are temporarily stored.

[Structure Identifier 17]

Figure 3:
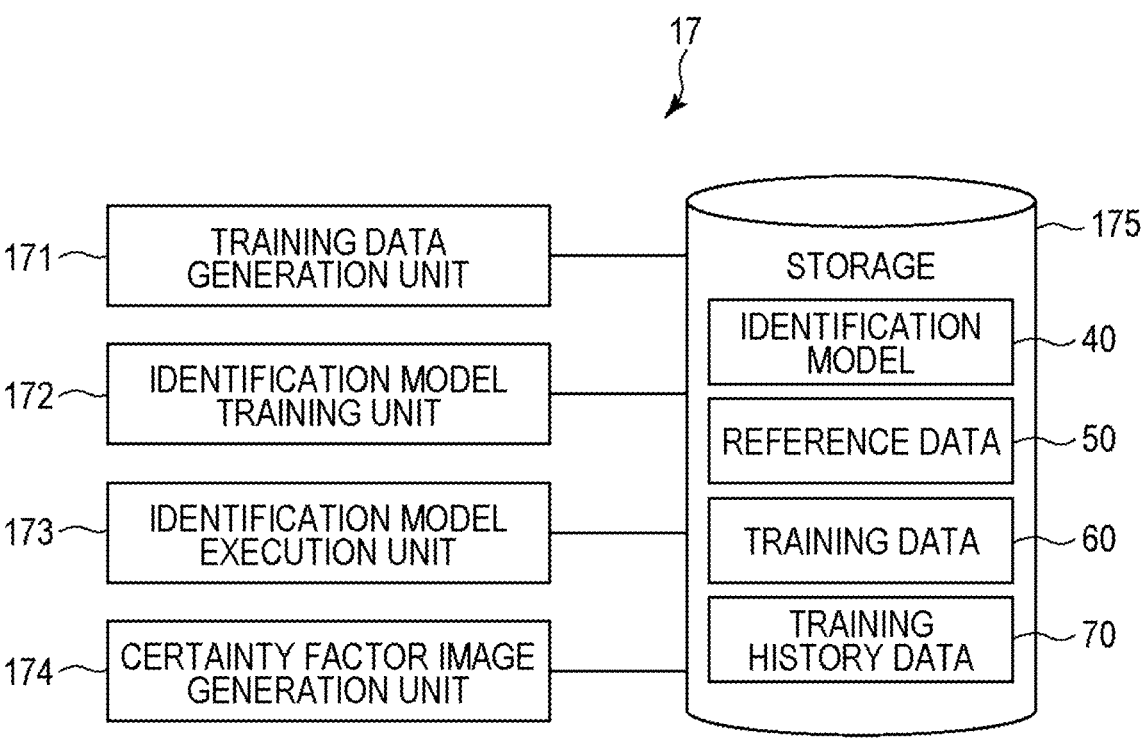
FIG. 3 is a diagram illustrating a configuration example of a structure identifier.

The structure identifier 17 will be described in detail below. FIG. 3 is a diagram illustrating a configuration example of the structure identifier 17. As illustrated in FIG. 3, the structure identifier 17 includes a training data generation unit 171, an identification model training unit 172, an identification model execution unit 173, a certainty factor image generation unit 174, and a storage 175. The storage 175 stores an identification model 40, reference data 50, training data 60, and training history data 70.

The training data generation unit 171 generates training data 60 for training the identification model 40 on the basis of a first image for generating the training data and the reference data 50 prepared in advance. The first image is extracted from, for example, an ultrasound image for training. The training data 60 is a data set in which a feature amount (for example, the luminance array) of a second image extracted from the first image is associated with information (for example, a certainty factor of a target corresponding to the central pixel block of the second image) regarding the certainty factor of the target. Note that the pixel block indicates each of divided regions obtained by dividing the image into a plurality of regions, and may include a pixel group including a plurality of pixels or include one pixel.

The identification model training unit 172 trains the identification model 40 by machine learning using the training data 60 generated by the training data generation unit 171. Specifically, the identification model training unit 172 corrects the identification model 40 so that, when an example problem (feature amount of the second image) of the training data 60 is input to the identification model 40, the answer (information regarding the certainty factor of the target) of the training data 60 is output.

The identification model execution unit 173 executes the trained identification model 40 to generate data for identifying a target in an ultrasound image for diagnosis. Note that the ultrasound image for diagnosis (hereinafter referred to as a diagnostic image) is not an ultrasound image for training but an image generated by the image acquirer 14 and input to the structure identifier 17 via the image processor 15 and the DSC 16 in a case where the user performs diagnosis using the ultrasound diagnostic apparatus 100.

For example, the identification model execution unit 173 extracts an identification image from the diagnostic image, and executes the identification model 40 using the identification image as an input, thereby acquiring information regarding the certainty factor of the target in the identification image as an output.

Note that the ultrasound image for training and the identification image are, for example, at least one of a composite image or a plurality of diagnostic images generated prior to the composite image currently displayed on the display 19, a mean value image generated by calculating a mean value of pixel values for each pixel of the plurality of diagnostic images generated previously, or a maximum value image generated based on a maximum value of pixel values for each pixel in the plurality of diagnostic images previously generated. The ultrasound image for training is stored in the storage 175 or the like.

The certainty factor image generation unit 174 generates a certainty factor image corresponding to the whole or a part of the diagnostic image (for example, a region surrounded by an ROI frame) on the basis of the output from the identification model execution unit 173. At this time, the certainty factor image generation unit 174 may remove noise included in the certainty factor image on the basis of a temporal change in information regarding the certainty factor obtained from temporally consecutive ultrasound images. Specifically, noise included in the certainty factor image can be removed by applying moving-average filter processing or median filter processing in the time axis direction. Furthermore, a region in which a change (steepness) in the information regarding the certainty factor exceeds a preset threshold may be detected as a noise region, and noise removal processing may be performed only for this noise region.

The storage 175 includes, for example, a nonvolatile semiconductor memory (so-called flash memory), a hard disk drive (HDD), or the like. The storage 175 may be a disk drive that reads and writes information by driving an optical disk such as a compact disc (CD), a digital versatile disc (DVD), or a Blu-ray disc (BD) ("Blu-ray" is a registered trademark), or a magnetic optical disk such as a magneto-optical disk (MO).

The storage 175 stores the identification model 40, the reference data 50, the training data 60, and the training history data 70 as described above. The training data 60 used for training the identification model 40 may be appropriately overwritten when the training data 60 is newly generated by the training data generation unit 171. The training history data 70 includes, for example, information such as the number of training data 60 used for training and training date and time.

Figure 4A:
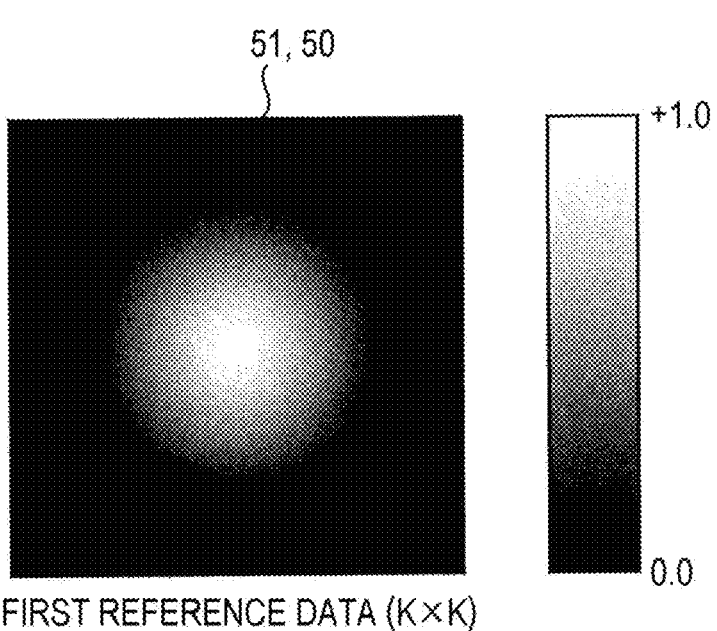
FIG. 4A is a diagram illustrating an example of reference data.
Figure 4B:
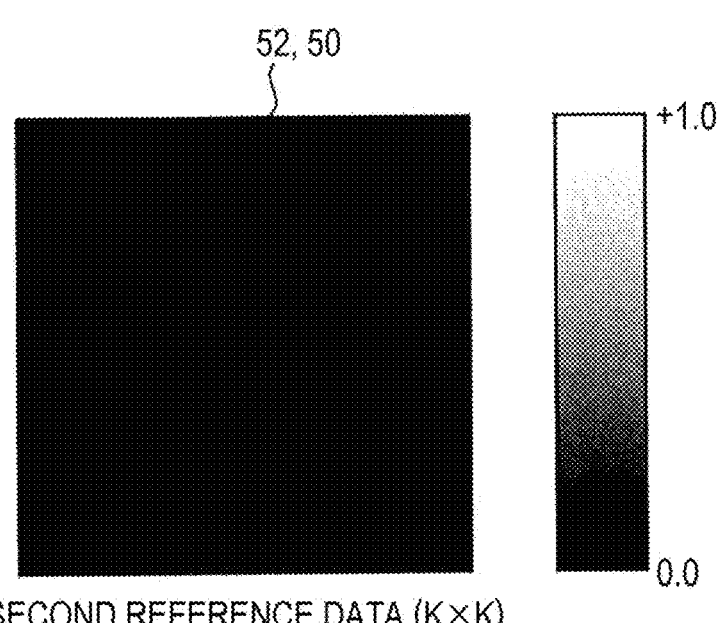
FIG. 4B is a diagram illustrating an example of reference data.

FIGS. 4A and 4B are diagrams illustrating an example of the reference data 50. As illustrated in FIGS. 4A and 4B, the reference data 50 includes first reference data 51 to be referred to when the target is included in the first image (ultrasound image for generating training data), and second reference data 52 to be referred to when the target is not included in the first image.

The first reference data 51 illustrated in FIG. 4A is referred to in a case where the target is visualized in the center of the first image, and is set in accordance with a circular Gaussian distribution with the certainty factor of the target being within a range from 0.0 to 1.0, for example.

The second reference data 52 indicates a certainty factor distribution in a case where there is no target in the first image (in a case where the first image is configured with a non-target). In the second reference data 52 illustrated in FIG. 4B, the certainty factor of the target corresponding to the entire region is set to 0. Noe that a plurality of first reference data 51 and a plurality of second reference data 52 may be prepared as necessary. For example, as the first reference data 51, data to be referred to when a longitudinal section of a nerve is visualized in the first image may be prepared. When there are multiple targets, second reference data for another target may be prepared as the second reference data 52.

Operation

An operation example of the image generation device 1 will be described below. First, processing for generating the identification model by the structure identifier 17 will be described in detail.

[Processing for Generating Identification Model]

Figure 5:
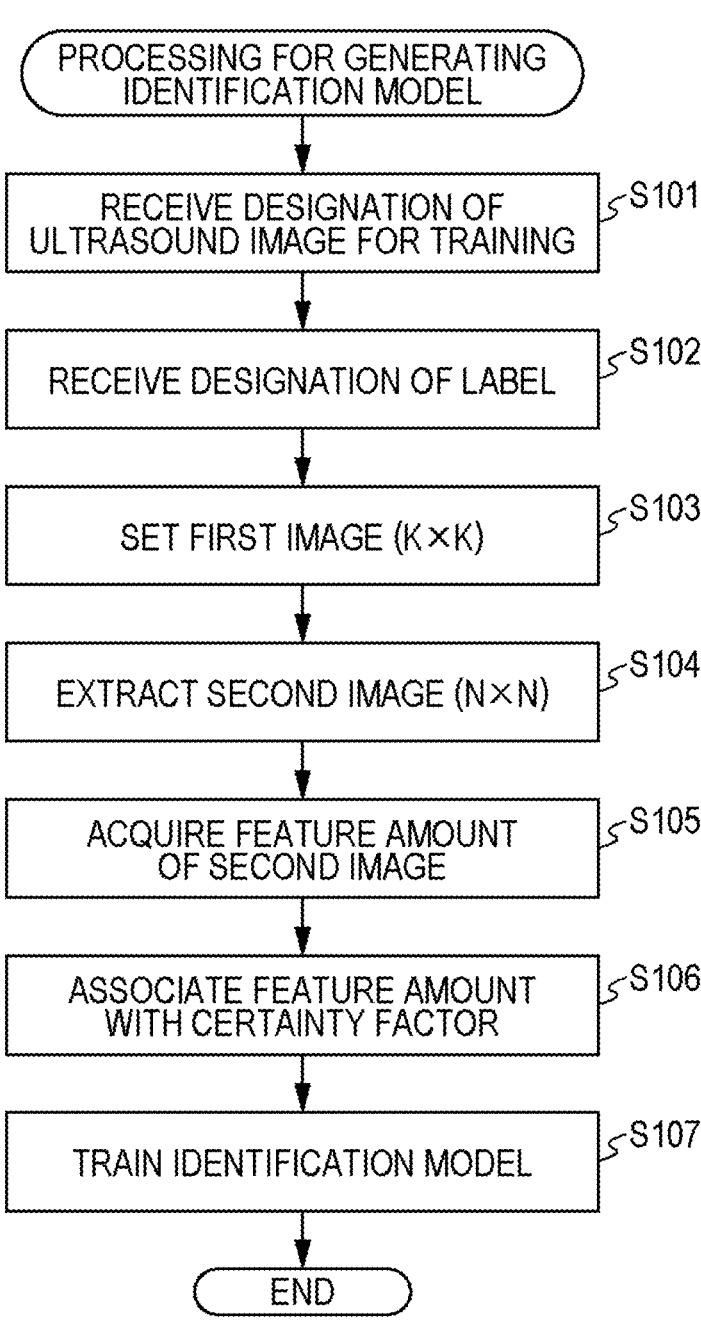
FIG. 5 is a flowchart illustrating an example of processing for generating an identification model for training an identification model.

FIG. 5 is a flowchart illustrating an example of processing for generating an identification model for training the identification model 40. This processing is performed, for example, when a training mode is selected by mode selection via the operation input unit 11.

In step S101, the training data generation unit 171 receives designation of an ultrasound image for training under the control of the controller 110. The ultrasound image for training is acquired in advance for training and stored in the storage 175, for example, and is read on the basis of an input operation performed by the user using the operation input unit 11. Furthermore, for example, an ultrasound image acquired at the time of past diagnosis may be applied as an ultrasound image for training.

In step S102, the training data generation unit 171 receives designation of a label under the control of the controller 110. The label has a first label designated when an object to be trained is a target and a second label designated when the object to be trained is a non-target, and one of the labels is selected on the basis of an input operation performed by the user via the operation input unit 11. When the first label is designated, the training data 60 is generated using the first reference data 51, and when the second label is designated, the training data 60 is generated using the second reference data 52.

Figure 6:
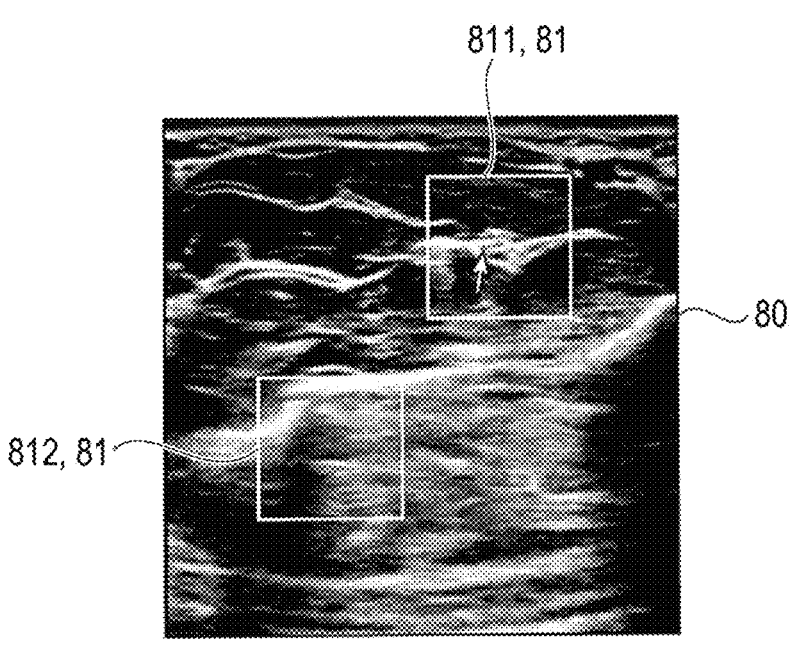
FIG. 6 is a diagram illustrating a relationship between an ultrasound image for training and a first image.

In step S103, the training data generation unit 171 sets the first image (the ultrasound image for generating training data) in the ultrasound image for training under the control of the controller 110. FIG. 6 is a diagram illustrating a relationship between an ultrasound image 80 for training and the first image 81. In the example illustrated in FIG. 6, the first image 81 includes a first image 811 that is set when a target is set as the object to be trained and a first image 812 that is set when a non-target is set as the object to be trained.

The first image 81 is set, for example, on the basis of an operation related to target designation by the user using the operation input unit 11. For example, when the user selects a region in which the target (or the non-target) is visualized in the ultrasound image 80, a region having a predetermined size around the region is set as the first image 81. Furthermore, for example, the size of a region (a white-outlined rectangular frame in FIG. 6) set as the first image 81 may be able to be designated on the basis of a user's operation.

Hereinafter, a case where the first label is designated in step S102 and the first image 811 including the target is set will be specifically described.

Figure 7A:
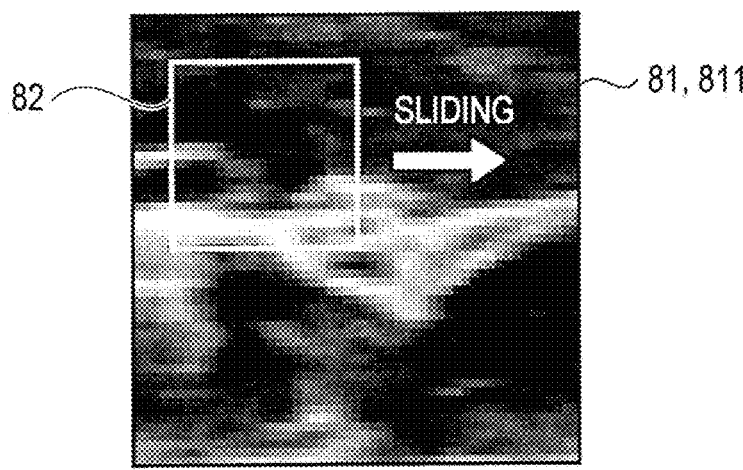
FIG. 7A is a diagram for describing a method for generating training data.
Figure 7B:
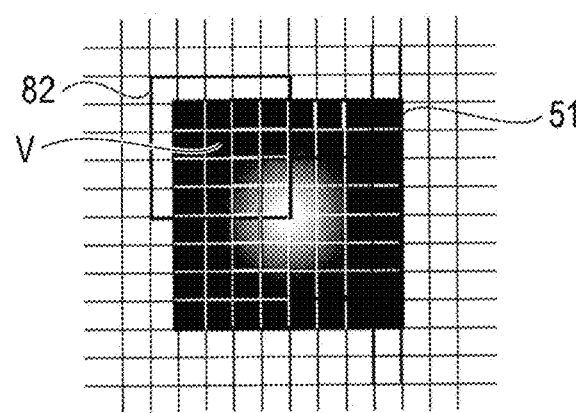
FIG. 7B is a diagram for describing the method for generating training data.
Figure 7C:
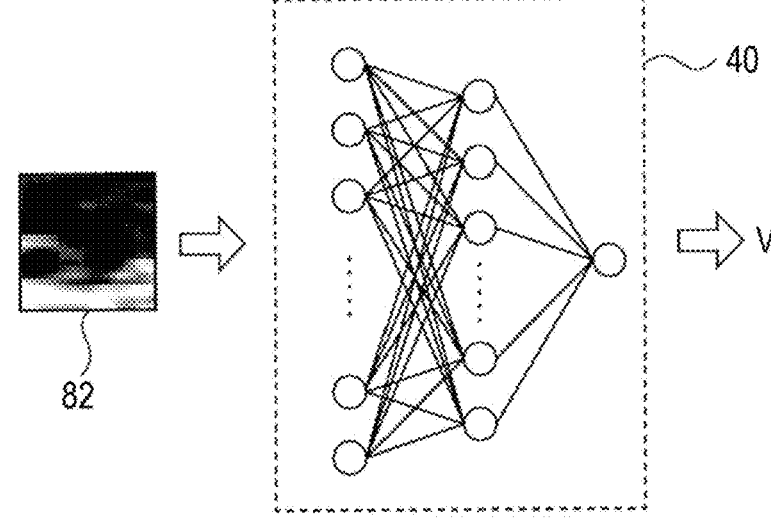
FIG. 7C is a diagram for describing the method for generating training data.

In step S104, the training data generation unit 171 extracts the second image 82 from the first image 811 under the control of the controller 110. FIGS. 7A, 7B, and 7C are diagrams for describing a method for generating training data. FIG. 7A is a diagram for describing the second image 82. The second image 82 is included in the first image 811 and serves as an input (example problem) of training data. For example, the second image 82 including N×N (N<M) pixel blocks is extracted from the first image 81 including M×M pixel blocks.

In step S105, the training data generation unit 171 acquires a feature amount of the second image 82 under the control of the controller 110. The feature amount of the second image 82 is, for example, a luminance array including luminance values for each pixel (or pixel block) of the second image 82.

In step S106, the training data generation unit 171 associates the feature amount of the second image 82 with the certainty factor of the target on the basis of the reference data 50 under the control of the controller 110.

Specifically, as illustrated in FIGS. 7A and 7B, the training data generation unit 171 compares the second image 82 with the first reference data 51, specifies a certainty factor V of the target corresponding to the central pixel block of the second image 82 from the first reference data 51, and associates the certainty factor V with the feature amount of the second image 82. FIG. 7B is a diagram illustrating the manner of specifying the certainty factor V of the target from the first reference data 51. At this time, the first reference data 51 is appropriately adjusted according to the size of the first image 81.

Due to the process of step S106, one set of training data 60 in which the feature amount of the second image 82 is associated with the certainty factor V of the target corresponding to the central pixel block of the second image 82 is generated. A plurality of sets of training data 60 is generated by performing the processes of steps S104 to S106 while sliding the extraction region of the second image 82 in the first image 81. For example, in a case where the reference data 50 includes K×K pixel blocks, the certainty factor of the target can be assigned to the feature amounts of K×K second images 82. That is, (K×K) training data can be generated by designating the first image 81 only once.

The training data 60 is generated by the above steps executed by the training data generation unit 171.

In step S107, the identification model training unit 172 trains the identification model 40 by machine learning using the generated training data 60 under the control of the controller 110. Specifically, the identification model training unit 172 corrects the identification model 40 so that, when the example problem (the feature amount of the second image 82) of the training data 60 is input to the identification model 40, the answer of the training data 60 (the certainty factor V of the target corresponding to the central pixel block of the second image 82) is output as illustrated in FIG. 7C. FIG. 7C is a diagram illustrating the manner of correcting the identification model 40 on the basis of the second image 82. The identification model 40 and the training history data 70 stored in the storage 175 are updated on the basis of the training result.

In a case where the identification model 40 is trained, a training history (for example, the number of training data used for training) of the identification model 40 is preferably displayed on the display 19. As a result, the user can grasp the degree of training of the identification model 40, and can learn how much training is required in the future in order to obtain sufficient accuracy during identification of the target using the identification model 40.

Note that, in the above description, a mode has been described in which the structure identifier 17 includes the training data generation unit 171, the identification model training unit 172, the identification model execution unit 173, the certainty factor image generation unit 174, and the storage 175, and the identification model is trained by these configurations. However, the present disclosure is not limited thereto.

The above-described processing for generating the identification model may not be performed by the image generation device 1 according to the present disclosure. For example, the structure identifier 17 may not include the identification model training unit, the identification model execution unit, and the certainty factor image generation unit. In this case, the structure identifier 17 acquires, from an external device outside the image generation device 1, the identification model generated by the external device. Note that a method similar to the method described above may be employed as a method for generating the identification model by the external device. In this case, the structure identifier 17 stores the identification model acquired from the outside of the image generation device 1 in the storage 175, and reads and uses the identification model stored in the storage 175 during processing for generating a composite image described below.

[Processing for Generating Composite Image]

The image generation device 1 generates a composite image using the identification model generated as described above or the identification model generated by the external device outside the image generation device 1. The processing for generating the composite image will be described in detail below.

Figure 8:
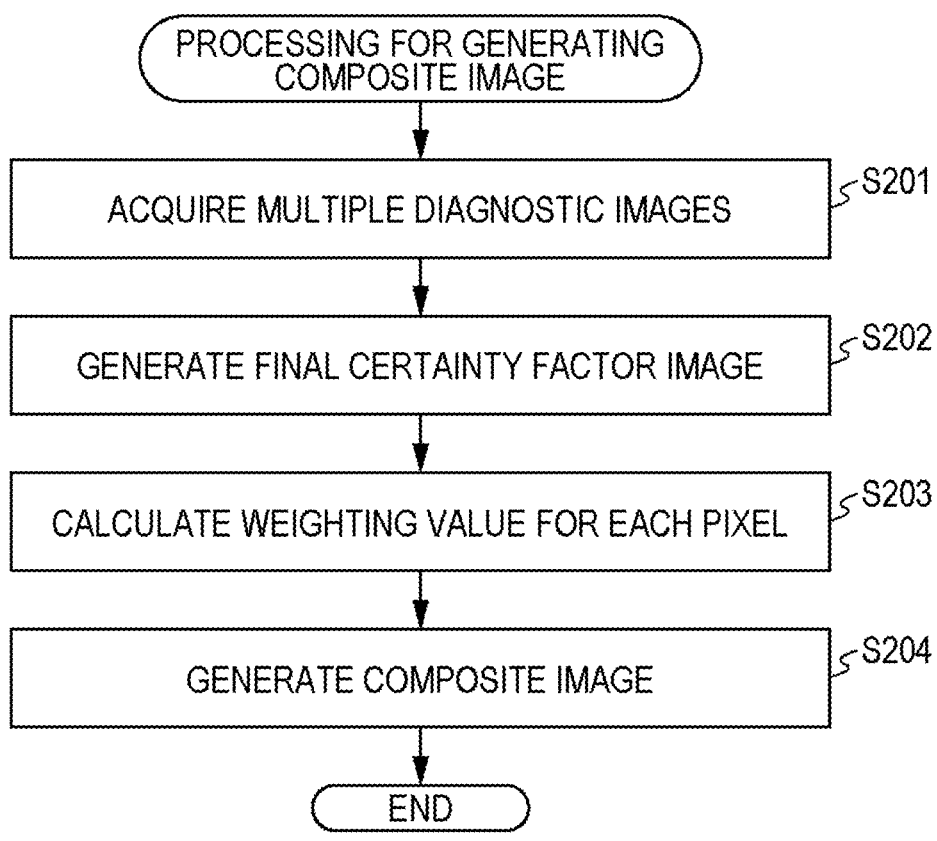
FIG. 8 is a flowchart illustrating an operation example when the image generation device generates a composite image.

FIG. 8 is a flowchart illustrating an operation example when the image generation device 1 generates a composite image.

In step S201, the controller 110 acquires a plurality of diagnostic images having different steering angles. More specifically, the controller 110 controls the transmission unit 12 to transmit an ultrasound wave at a predetermined steering angle from the ultrasound probe 2, and controls the reception unit 13 to acquire a reception signal corresponding to the reflected ultrasound wave (ultrasound echo) received by the ultrasound probe 2. Then, the controller 110 controls the image acquirer 14 to generate a B-mode ultrasound image based on the reception signal. The controller 110 performs the above process multiple times while changing the steering angle, thereby acquiring a plurality of diagnostic images having different steering angles.

In step S202, the structure identifier 17 generates a final certainty factor image on the basis of the plurality of diagnostic images under the control of the controller 110. The final certainty factor image indicates a certainty factor image used for calculating a weighting value in step S203. As a method for generating the final certainty factor image based on the plurality of diagnostic images, at least the following two methods can be employed.

The first method is for generating a plurality of certainty factor images on the basis of each of the plurality of diagnostic images, and then combining the plurality of certainty factor images to generate a final certainty factor image. The second method is for generating a maximum value image or a mean value image of the plurality of diagnostic images and directly generating a final certainty factor image based on the maximum value image or the mean value image. The maximum value image refers to a single image obtained by extracting the maximum pixel value for each identical pixels of a plurality of diagnostic images and setting the extracted maximum pixel values as pixel values. The mean value image refers to a single image obtained by calculating a mean value of pixel values of a plurality of diagnostic images for each pixel and setting the calculated mean values as pixel values. The second method does not generate a plurality of certainty factor images, and thus, the final certainty factor image can be acquired with a smaller number of processes.

The detail of the processing for generating the plurality of certainty factor images on the basis of each of the plurality of diagnostic images with the first method is as described below, for example. The identification model execution unit 173 of the structure identifier 17 extracts an identification image from each diagnostic image and inputs a feature amount (for example, the luminance array) of the identification image to the identification model 40. Then, the identification model execution unit 173 acquires the certainty factor corresponding to the central pixel block of the identification image from the identification model 40 as an output. In addition, the certainty factor image generation unit 174 acquires the certainty factor for the entire diagnostic image to generate a certainty factor image.

Figure 9:
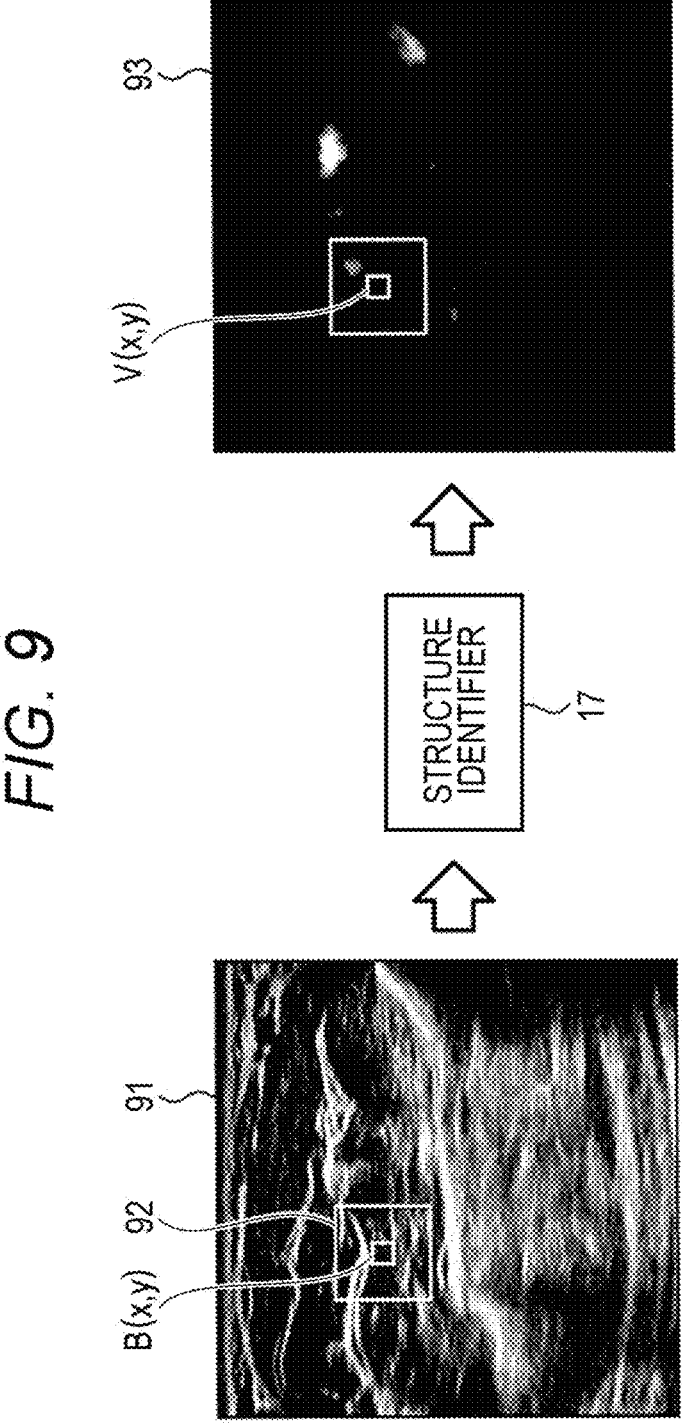
FIG. 9 is a schematic diagram illustrating a manner of acquiring a certainty factor by the structure identifier.

FIG. 9 is a schematic diagram illustrating the manner of acquiring a certainty factor by the structure identifier 17. FIG. 9 schematically illustrates a state in which an identification image 92 set inside a diagnostic image 91 is set, and a certainty factor V(x, y) corresponding to the luminance array B(x, y) of the pixel block in the central portion of the identification image 92 is acquired. The controller 110 causes the certainty factor image generation unit 174 of the structure identifier 17 to repeat this process and acquires the certainty factor of the entire diagnostic image 91, thereby generating a certainty factor image 93 corresponding to the entire diagnostic image 91. Note that the certainty factor image may be generated so as to correspond to a part of the diagnostic image.

Then, the certainty factor image generation unit 174 generates a final certainty factor image on the basis of the plurality of certainty factor images. As a method for generating a final certainty factor image on the basis of a plurality of certainty factor images, there is a method for extracting or calculating a maximum value, a mean value, or a minimum value for each pixel of the plurality of certainty factor images, and generating a final certainty factor image having the extracted values as pixel values. Which one of the maximum value, the mean value, and the minimum value for each pixel of the plurality of certainty factor images is used can be selected by the user's operation using the operation input unit 11.

When the final certainty factor image is generated with the first method, the characteristics of the final certainty factor image vary depending on whether the maximum value, the mean value, or the minimum value for each pixel of the plurality of certainty factor images is used. When the maximum value is used, the sensitivity, that is, the degree in which a region including the target can be detected is relatively high, and a degree of false-positive, that is, the degree in which a region including no target is detected as the target is also relatively high. The sensitivity and the degree of false-positive are relatively low when the minimum value is used, and the sensitivity and the degree of false-positive when the mean value is used are lower than those when the maximum value is used and higher than those when the minimum value is used.

With the second method, the certainty factor image generation unit 174 causes the identification model execution unit 173 of the structure identifier 17 to extract an identification image from a maximum value image or a mean value image generated on the basis of the plurality of diagnostic images, input a feature amount (for example, the luminance array) of the identification image to the identification model 40, and acquire the certainty factor as an output. In addition, the certainty factor image generation unit 174 acquires the certainty factor for the entire maximum value image or mean value image to generate a final certainty factor image.

In the second method, which one of the maximum value image and the mean value image is used can be selected by the user's operation using the operation input unit 11, for example.

The characteristics of the final certainty factor image vary depending on whether the maximum value image or the mean value image is used in the second method. When the maximum value image is used, the sensitivity is relatively high, and the degree of false-positive is relatively high. When the mean value is used, the sensitivity and the degree of false-positive are lower than those when the maximum value is used.

When the final certainty factor image is generated in step S202, which of the first method and the second method described above is adopted can be selected by a user's operation using the operation input unit 11, for example.

In addition, in step S202, it is preferable that the selection of which one of the maximum value, the mean value, and the minimum value for each pixel of the plurality of certainty factor images is used in a case where the first method is adopted, and the selection of which one of the maximum value image and the mean value image is used in a case where the second method is adopted are performed according to the purpose of diagnosis.

Specific examples will be described. For example, in a case where the user inserts a puncture needle into the subject while viewing the composite image displayed by the image generation device 1 and injects an anesthetic solution into the vicinity of the nerve region, it is preferable that the degree of false-positive in a region other than the nerve in the composite image is lowered. In this case, it is preferable to use a mean value in the first method and to use a mean value image in the second method.

In addition, in a case where, for example, the user inserts a puncture needle into the subject while viewing a composite image displayed by the image generation device 1 and injects a liquid medicine into a blood vessel region, it is preferable that the sensitivity is increased so that a nerve region that should not be punctured can be reliably detected. In this case, it is preferable to use the maximum value in the first method, and to use the maximum value image in the second method.

Note that, when the final certainty factor image is generated in step S202 in a case where there are multiple targets, the final certainty factor image for each target is generated using a different identification model for each target. Here, whether to use the first method or the second method for generating the final certainty factor image may be set for each target. Furthermore, in a case where the first method is used, which one of the maximum value, the mean value, and the minimum value for each pixel of the plurality of certainty factor images is used may be set for each target. Further, when the second method is used, which one of the maximum value image and the mean value image is used may be set for each target. As a result, the manner of emphasis in the composite image can be made different for each target, and the composite image according to the purpose of diagnosis can be obtained.

In the description of step S202, the structure identifier 17 generates the final certainty factor image on the basis of the plurality of diagnostic images under the control of the controller 110. The plurality of diagnostic images used by the structure identifier 17 to generate the final certainty factor image may be, for example, images which have not yet been subjected to signal format conversion by the DSC 16 or images which have been subjected to the signal format conversion by the DSC 16. In the case of using images which have not yet been subjected to the format conversion by the DSC 16, the structure identifier 17 may output the generated certainty factor image to the DSC 16, and may generate a final certainty factor image by using an image which has been subjected to the format conversion by the DSC 16.

In step S203, the image combiner 18 calculates a weighting value when combining the plurality of diagnostic images on the basis of the final certainty factor image under the control of the controller 110. The weighting value is from 0 to 1, and is set for each pixel of the diagnostic image. The weighting value is set to the certainty factor for each pixel of the final certainty factor image corresponding to each pixel of the diagnostic image Note that, in the present embodiment, the value of each pixel of the final certainty factor image is set as a weighting value for the pixel. However, for example, the weighting value may be calculated on the basis of the value of each pixel of the final certainty factor image using a predetermined calculation method.

In step S204, the image combiner 18 generates a composite image on the basis of the plurality of diagnostic images having different steering angles from each other and the weighting value under the control of the controller 110. The composite image is generated by α-blending a maximum value image obtained by extracting a maximum value for each pixel of the plurality of diagnostic images and using the extracted maximum values as pixel values, and a mean value image obtained by calculating a mean value for each pixel of the plurality of diagnostic images and using the calculated mean values as pixel values, using a weighting value.

Figure 10:
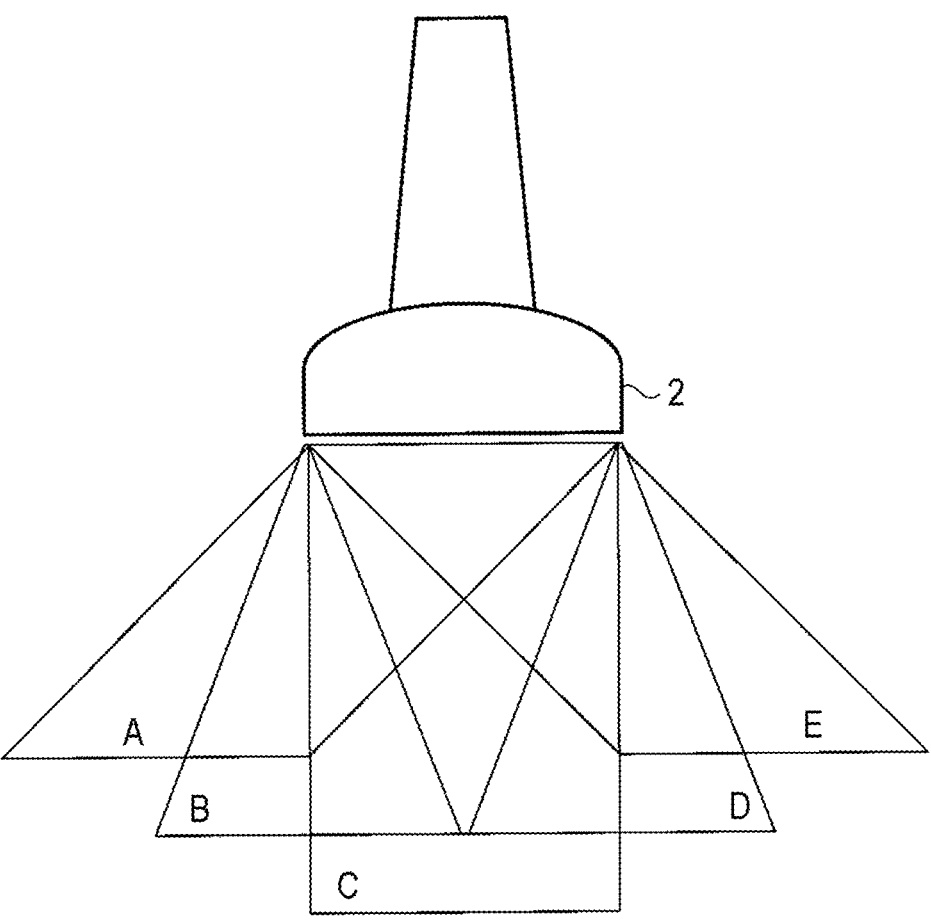
FIG. 10 is a diagram schematically illustrating a state of combining a plurality of diagnostic images having different steering angles.

The processing for generating the composite image will be described in detail with reference to FIG. 10. FIG. 10 is a diagram schematically illustrating a state of combining a plurality of diagnostic images having different steering angles. FIG. 10 illustrates five diagnostic images A, B, C, D, and E having steering angles different from each other.

In this case, the image combiner 18 calculates a maximum value Max(A, B, C, D, E) of pixel values of the same pixels in the diagnostic images A, B, C, D, and E and a mean value Mean(A, B, C, D, E) of the pixel values of the same pixels in the diagnostic images A, B, C, D, and E. Then, the image combiner 18 performs a blending processing using the weighting value α corresponding to the pixel value of the pixel of the final certainty factor image. Therefore, each pixel value Data of the composite image obtained by the image combiner 18 is expressed by following Formula (1).

[Mathematical Formula 1]

$$\text{Data}=\alpha*\text{Max}(A, B, C, D, E)+(1-\alpha)*\text{Mean}(A, B, C, D, E) \qquad (1)$$

As another combining method, the image combiner 18 may add a weight to each of the pixel values of the same pixels in the diagnostic images A, B, C, D, and E and then add the resultant values to calculate each pixel value Data of the composite image as expressed in following Formula (2).

[Mathematical Formula 2]

$$\text{Data}=\alpha 1*A+\alpha 2*B+\alpha 3*C+\alpha 4*D+\alpha 5*E \qquad (2)$$

In the case of using Formula (2), it is not necessary to generate a final certainty factor image, and it is only sufficient that the weighting values $\alpha 1$, $\alpha 2$, $\alpha 3$, $\alpha 4$, and $\alpha 5$ are determined on the basis of a plurality of certainty factor images generated on the basis of each of the plurality of diagnostic images.

When the processing described above is performed for all pixels, a composite image is generated. By generating the composite image by the spatial compounding in this manner, noise, particularly speckle noise, can be reduced, and a structure having anisotropy with respect to the transmission ultrasound wave can be accurately detected. Furthermore, since the weighting value based on the certainty factor image is used for generating the composite image, the structure set as the target can be accurately detected, and noise other than the target or a situation in which the structure is erroneously emphasized can be avoided.

Note that the method for calculating the weighting value is not limited to the above-described calculation method (method using the final certainty factor image), and the weighting value may be calculated by a different method. When the weighting value is also calculated by a different method, for example, the larger one of the weighting value calculated by the above-described calculation method and the weighting value calculated by the different method may be adopted.

Note that the processing for generating the composite image described above is performed for each frame, and the composite image is updated and displayed for each frame on the display 19, whereby the user can perform diagnosis based on the ultrasound image that is a moving image and that smoothly shows the movement of the structure.

Effects

The configuration and operation of the image generation device 1 according to the present disclosure have been described above. In the image generation device 1 according to the present disclosure, the composite image is generated using the weighting value based on the certainty factor image, so that a pixel having a high certainty factor of the target can be emphasized, and the visibility of the target when the composite image is displayed on the display 19 is improved. Furthermore, noise other than the target or a situation in which a structure is erroneously emphasized can be avoided.

In the image generation device 1 according to the present disclosure, the certainty factor image used for generating the composite image is generated on the basis of an image different from the composite image currently displayed on the display 19, such as a past composite image, a past diagnostic image, or a maximum value image or a mean value image generated on the basis of the past diagnostic image. Therefore, it is possible to generate a new composite image in a short time as compared with a case where the certainty factor image is generated using the composite image currently displayed on the display 19 and a plurality of current diagnostic images is combined on the basis of the generated certainty factor image. As a result, even when it takes time to detect the target, a composite image in which the user can easily visually recognize the target can be quickly generated.

The present invention is suitable for an image generation device that combines a plurality of ultrasound images.

Although embodiments of the present invention have been described and illustrated in detail, the disclosed embodiments are made for purposes of illustration and example only and not limitation. The scope of the present invention should be interpreted by terms of the appended claims.

What is claimed is:

1. An image generation device comprising:

an image acquirer that acquires a plurality of ultrasound images generated on the basis of a plurality of reception signals respectively corresponding to reflected ultrasound waves of transmission ultrasound waves transmitted in a plurality of different transmission directions;

a processor that generates a plurality of certainty factor images on the basis of the plurality of ultrasound images, each of the plurality of certainty factor images including pixel values that indicate certainty factors, each of the certainty factors indicating likelihood of being an object to be identified and being acquired by inputting the plurality of ultrasound images that has been acquired to an identification model, the identification model being configured to receive an identification image extracted from an ultrasound image and output a certainty factor that is an index indicating likelihood that a certain region in the identification image is a target, wherein the identification model is constructed by supervised machine learning in which a relationship between a luminance array of the ultrasound image and information regarding a certainty factor of the target is trained as training data using a machine learning algorithm, the luminance array including luminance values for each pixel or pixel block of the ultrasound image;

generates a final certainty factor image on the basis of the plurality of certainty factor images, the final certainty factor image including pixel values that indicate final certainty factors, the pixel values of the final certainty factor image being mean values, maximum values or minimum values calculated, on a pixel-by-pixel basis, from the pixel values of the plurality of certainty factor images; and an image combiner that determines weighting values on the basis of the final certainty factor image, wherein each of the weighting values is set to the final certainty factor for each pixel of the final certainty factor image corresponding to each pixel of the plurality of ultrasound images; and generates a composite image on the basis of the plurality of ultrasound images and the weighting values.

2. The image generation device according to claim 1, wherein the trained identification model is a neural network.

3. The image generation device according to claim 1, further comprising a display that displays the composite image, wherein the processor inputs an image different from the composite image displayed on the display to the identification model.

4. The image generation device according to claim 1, wherein the processor inputs, to the identification model, the composite image generated prior to the composite image currently displayed on the display, the plurality of ultrasound images generated prior to the composite image currently displayed on the display, and an image generated by calculating a mean value or a maximum value of pixel values for each pixel of the plurality of ultrasound images generated prior to the composite image currently displayed on the display.

5. The image generation device according to claim 1, wherein the object to be identified is a nerve, a fascia, a blood vessel, or a puncture needle.

6. The image generation device according to claim 1, wherein the image combiner determines the weighting values according to a type of the object to be identified.

7. The image generation device according to claim 1, wherein the image combiner further generates a maximum value image on the basis of the plurality of ultrasound images, the maximum value image including pixel values that are extracted, on a pixel-by-pixel basis, from pixel values of the plurality of ultrasound images;

generates a mean value image on the basis of the plurality of ultrasound images, the mean value image including pixel values that are calculated, on a pixel-by-pixel basis, from the pixel values of the plurality of ultrasound images; and calculates, on a pixel-by-pixel basis, pixel values of the composite image on the basis of the pixel values of the maximum value image, the pixel values of the mean value image, and weighting values.

8. The image generation device according to claim 1, wherein the certainty factor of the target and a region around the target is larger than the certainty factor of a region other than the target and the region around the target.

9. The image generation device according to claim 1, wherein the training data is a data set in which the luminance array of a second image extracted from the ultrasound image is associated with the information regarding the certainty factor of the target, and the information regarding the certainty factor of the target is a certainty factor of the target corresponding to a central pixel block of the second image.

10. The image generation device according to claim 1, wherein the processor corrects the identification model so that, when an example problem of the training data is input to the identification model, an answer of the information regarding the certainty factor of the target of the training data is output.

11. The image generation device according to claim 1, wherein the identification model is trained by:

receiving designation of the ultrasound image, receiving designation of one of a first label and a second label on the basis of an input operation performed by a user, the first label being designated when an object to be trained is the target, the second label being designated when the object trained is a non-target, generating the training data using a first reference data when the first label is designated, and generating the training data using a second reference data when the second label is designated, wherein the first reference data is set in accordance with a circular Gaussian distribution with the certainty factor of the target within a range from 0.0 to 1.0, and in the second reference data, the certainty factor of the target corresponding to an entire region is set to 0.

12. An image generation method executed by a computer included in an image generation device, wherein the computer executes:

acquiring a plurality of ultrasound images generated on the basis of a plurality of reception signals respectively corresponding to reflected ultrasound waves of transmission ultrasound waves transmitted in a plurality of different transmission directions;

generating a plurality of certainty factor images on the basis of the plurality of ultrasound images, each of the plurality of certainty factor images including pixel values that indicate certainty factors, each of the certainty factors indicating likelihood of being an object to be identified and being acquired by inputting the plurality of ultrasound images that has been acquired to an identification model, the identification model being configured to receive an identification image extracted from an ultrasound image and output a certainty factor that is an index indicating likelihood that a certain region in the identification image is a target, wherein the identification model is constructed by supervised machine learning in which a relationship between a luminance array of the ultrasound image and information regarding a certainty factor of the target is trained as training data using a machine learning algorithm, the luminance array including luminance values for each pixel or pixel block of the ultrasound image;

generating a final certainty factor image on the basis of the plurality of certainty factor images, the final certainty factor image including pixel values that indicate final certainty factors, the pixel values of the final certainty factor image being mean values, maximum values or minimum values calculated, on a pixel-by-pixel basis, from the pixel values of the plurality of certainty factor images;

determining weighting values on the basis of the final certainty factor image, wherein each of the weighting values is set to the final certainty factor for each pixel of the final certainty factor image corresponding to each pixel of the plurality of ultrasound images; and generating a composite image on the basis of the plurality of ultrasound images and the weighting values.

13. A non-transitory recording medium storing a computer readable program causing a computer to perform:

acquiring a plurality of ultrasound images generated on the basis of a plurality of reception signals respectively corresponding to reflected ultrasound waves of transmission ultrasound waves transmitted in a plurality of different transmission directions;

generating a plurality of certainty factor images on the basis of the plurality of ultrasound images, each of the plurality of certainty factor images including pixel values that indicate certainty factors, each of the certainty factors indicating likelihood of being an object to be identified and being acquired by inputting the plurality of ultrasound images that has been acquired to an identification model, the identification model being configured to receive an identification image extracted from an ultrasound image and output a certainty factor that is an index indicating likelihood that a certain region in the identification image is a target, wherein the identification model is constructed by supervised machine learning in which a relationship between a luminance array of the ultrasound image and information regarding a certainty factor of the target is trained as training data using a machine learning algorithm, the luminance array including luminance values for each pixel or pixel block of the ultrasound image;

generating a final certainty factor image on the basis of the plurality of certainty factor images, the final certainty factor image including pixel values that indicate final certainty factors, the pixel values of the final certainty factor image being mean values, maximum values or minimum values calculated, on a pixel-by-pixel basis, from the pixel values of the plurality of certainty factor images;

determining weighting values on the basis of the final certainty factor image, wherein each of the weighting values is set to the final certainty factor for each pixel of the final certainty factor image corresponding to each pixel of the plurality of ultrasound images; and generating a composite image on the basis of the plurality of ultrasound images and the weighting values.

* * * * *